(12) United States Patent
St. Martin et al.

(10) Patent No.: US 7,435,873 B2
(45) Date of Patent: Oct. 14, 2008

(54) **IDENTIFICATION OF SOYBEANS HAVING RESISTANCE TO *PHYTOPHTHORA SOJAE***

(75) Inventors: Steven St. Martin, Columbus, OH (US); Anne Dorrance, Wooster, OH (US); Kara Burnham, Portland, OR (US); Ron Fioritto, Wooster, OH (US); David Francis, Wooster, OH (US); Stuart G. Gordon, Stow, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 247 days.

(21) Appl. No.: 10/778,018

(22) Filed: Feb. 12, 2004

(65) Prior Publication Data

US 2004/0261144 A1 Dec. 23, 2004

Related U.S. Application Data

(63) Continuation-in-part of application No. 10/436,376, filed on May 12, 2003.

(60) Provisional application No. 60/379,304, filed on May 10, 2002, provisional application No. 60/427,637, filed on Nov. 19, 2002.

(51) Int. Cl.
*A01H 1/04* (2006.01)
(52) U.S. Cl. ..................... 800/267; 800/266
(58) Field of Classification Search ............ 800/266, 800/267, 312
See application file for complete search history.

(56) References Cited

U.S. PATENT DOCUMENTS

| 5,491,081 | A | 2/1996 | Webb |
| 6,162,967 | A | 12/2000 | Webb |
| 6,538,175 | B1 | 3/2003 | Webb |
| 2002/0129402 | A1 | 9/2002 | Lightfoot et al. |
| 2006/0041955 | A1 | 2/2006 | Godwin et al. |

OTHER PUBLICATIONS

Demirbas et al. 2001. Crop Sci. 41; 1220-1227.*
Westman et al. 1998. Theor. Appl. Genet. 96: 272-281.*
Concibido et al. 1997. Crop Sci. 37: 258-264.*
Van Ooijen et al. 1994. Theor. Appl. Genet. 89: 1007-1013.*
Michelmore et al. 1991. Proc. Natl. Acad. Sci. 88: 9828-9832.*
Lee et al. 1996. Theor. Appl. Genet. 92:516-523.*
Cregan et al. 1999. Crop Sci. 39: 1464-1490.*
Hegstad et al. 1998. Crop Sci. 38: 50-55.*
Cregan et al. 1999. Crop Sci. 39: 1464-1490.*
"New Sources of Resistance to *Phytophthora sojae* in the Soybean Plant Introductions" by Schmitthenner, et al., World Soybean Research Conference VI, pp. 522-523.
"*Rps*8, A New Locus in Soybean Resistance to *Phytophthora sojae*" by Burnham, et al., *Crop Sci.* 43:101-105(2003).

"New Sources of Resistance to *Phytophthora sojae* in the Soybean Plant Introductions" by Dorrance, et al. *Plant Disease*, Dec. 2000, 1303-1308.
"Genetic Diversity Patterns among Phytophthora Resistant Soybean Plant Introductions Based on SSR Markers" by Burnham, et al., *Corp Sci.*, 43:338-343 (2002).
"Reactions of Soybean Plant Introductions (PI273483 to PI427107) Following Innoculation with *Phytophthora sojae*" by Dorrance, et al., Ohio Agricultural Research and Development Center, Research Bulletin 1193, Jun. 2001.
"A new locus in soybean for resistance to *Phytophthora sojae*" by Burnham, et al., *Phytopatholy*, 92:S10-11; Abstract for APS Meetings in Milkwaukee, WI, Jul. 2002.
Evaluation of the USDA Soybean Germplasm Collection: Maturity Groups 000 to IV (PI 273.483 to PI 427.107), United States Department of Agriculture, Technical Bulleting No. 1718.
International Search Report received from the International Examining Authority dated Oct. 28, 2003.
Burnham, K.D., Quantitative trait loci for partial resistance to *Phytophthora sojae* in soybeans, Abstract, Crop. Science 92:S11, (2002).
OSU-OARDC Pages, Plant Germplasm Release Guidelines, pp. 11-18.
St. Martin et al., Registration of 'Darby' Soybean, Registration of 'Kottman'Soybean and Registration of HS93-4118 Soybean, (Crop. Sci. 41: 590-591, Mar.-Apr. 2001).
Soybean Growth and Development, 5 pages printout from http://www.extension.umn.edu/distribution/cropsystems/components/5701a.html, Jun. 5, 2002.
Lande, R., et al., Efficiency of Marker-Assisted Selection in the Improvement of Quantitative Traits, Genetics 124:743-756, Mar. 1990.
Abney, T.S., Melger, J.C., Richards, T.L., Scott, D.H., Grogan, J. and Young, J., 1997, New races of *Phytophthora sojae* with Rps1-d virulence, Plant Dis. 81:653-655.
Anderson, T.R., and Buzzel, R.I., 1992, Inheritance and linkage of the Rps7 gene for resistance to Phytophthora rot of soybean, Plant Dis. 76: 958-959.
Athow K.L., Laviolette, F.A., Mueller, E.H. and Wilcox, J.R., 1980, A new major gene for resistance to Phytophthora megasperma var. sojae in soybean, Phytopathology 70:977-980.

(Continued)

*Primary Examiner*—David H. Kruse
*Assistant Examiner*—Keith O. Robinson
(74) *Attorney, Agent, or Firm*—Calfee Halter & Griswold LLP

(57) ABSTRACT

The invention provides soybean plants having a novel determinant, Rps8, for resistance to *Phytophthora sojae*. The invention also provides methods for identifying germplasms that are either heterozygous or homozygous for Rps8 using marker assisted selection. Genetic markers with known chromosomal location that are associated with the Rps8 gene are used to confirm Rps8-derived *Phytophthora sojae* resistance in germplasms. Marker assisted selection also used when introgressing Rps8-derived soybean *Phytophthora sojae* resistance into non-resistant soybean germplasm or less resistant soybean germplasms.

30 Claims, 1 Drawing Sheet

OTHER PUBLICATIONS

Athow, K.L. and Laviolette, F.A., 1982, Rps6, a major gene for resistance to *Phytophthora megasperma* f. sp. Glycinea in soybena, Phytopathology 72: 1564-1567.

Bernard, R.L., Smith, P.E., Kaufmann, M.J. and Schmitthenner, A.F., 1957, Inheritance of resistance to Phytophthora root and stem rot in soybean, Agron, J. 49:391.

Briggs, F.N., Knowles, P.F., Introduction to Plant Breeding, Reinhold Publication Corp., New York, NY 1967.

Buzzell, R.I. and Anderson, T.R.., 1981, Another major gene for resistance to *Phytophthora megasperma* var. *sojae* in soybeans, Soybean Genet, Newsl. 8:30-33.

Diers, BW, Mansur, L, Imsande, J, Shoemaker, RC, Mapping Phytophthora Resistance Loci in Soybean with Restriction Fragment Length Polymorphism Markers Crop Sci 32: 377-383 '92.

Dorrance, A.E., McClure, S.A. and de Silva, A., 2003 Pathogenic diversity of *Phytophthora sojae* in Ohio soybean fileds, Plant Dis. 87:139-146.

Erwin et al., eds, Phytophthora, 1983, General resistance mechanisms against P sojae include structural features of the host, preformed chemical inhibitors, induced structural (continued from previous line) barriers, hypersensitive reactions and phytoalexins.

Kaitany, R.C., Hart, L.P. and Safir, G.R., 2001, Virulence composition of *Phytophthora sojae* in Michigan, Plant Dis. 85:1103-1106.

Kilen, T.C., Hartwig, E.E. and Keeling, B.L., 1974, Inheritance of a second major gene for resistance to Phytophthra root rot in soybeans, Crop. Sci. 14:260-262.

Kurle, J.E. And E.M. ElAraby, 2001, Changing composition of *Phytophthora sojae* races in Minnesota soils, Phytopathology 91:S51.

Leitz, R.A., G.L. Hartman, W.L. Pedersen and C.D. Nickell, 2000, Races of *Phytophthora sojae* on Soybean in Illinois, Plant. Dis. 84:487.

Mueller, E.H., Athow, K.L., and Laviolette, F.A., 1978, Inheritance of resistance to four physiologic races of Phytophthora megasperms var. sojae, Phytopathology 68:1318-1322.

Schmitthenner, A.F., 1985, Problems and progress in control of Phytophthora root rot of soybean, Plant Dis. 69:362-368.

Schmitthenner A.F. Hobe, M. and Bhat, R.G., 1994 *Phytophthora sojae* races in Ohio over a 10-year interval, Plant Dis. 78-269-276.

Tijssen, Overview of Principles of Hybridization and the Strategy of Nucleic Acid Probe Assays, Laboratory Techniques in Biochemistry and mOlecular Bioilogy-Hybridization with Nucleic Acid Probes, Part I, Chapter 2, Elseviver, NY 1993.

U.S. Dept. of Agriculture, Technical Bulletin of 1987 reprting that PI 399073 was resistant to Phytophthora.

van Ooijen, J.W. and Voorips, R.E., 2001, JointMap® 3.0, Software for the calculation of genetic linkage maps, Plant Research International, Wageningen, the Netherlands.

Wrather, J.A., Anderson, T.R., Arsyand, D.M., Tan, Y., Ploper, L.D., Porta-Puglia, JA., Ram, H.H. and Yorinori, J.R., 2001, Soybean disease loss estimates for the top ten soybean-producting countries in 1998, Can. J. Plant Pathol. 23:115-121.

Yang, X.B., Ruff, R.L., Meng, X.Q. and Workneh, F., 1996 Races of *Phytophthora sojae* in Iowa soybean fields, Plant Dis., 80:1418-1420.

Shoemaker, R.C., Cregan, P.B., Vodkin, L., "Soybean Genomics"(2003), American Society of Agronomy Monograph Series. p. 235-255.

Song, Q. J., et al., "A new integrated genetic linkage map of the soybean", *Theor Appl Genet*, (2004), vol. # 109, p. 122-128.

Partial International Search Report from PCT/US05/04651.

Gordon, Stuart G., et al., "Rsps8 Maps to a Resistance Gene Rich Region on Soybean Molecular Linkage Group F", Crop. Sci. 46:168-173, 2006, pp. 168-173.

Hegstad, J.M., et al., Identifying Resistance to *Phytophthora sojae* in Selected Soybean Accessions Using RFLP Techniques, Crop. Sci. 38: 50-55, 1998.

Pioneer, a Dupont Company, "Using Molecular Markers in Plant Genetics Research", 4 pgs.

USDA, ARS, National Genetic Resource program. Germplasm Resource Information Network—(GRIN_[online database] National Germplasm Resources Laboratory, Beltsville, MD available: http://www.ars-grin.gov/cgi-bin/npgs/acc/display.pl?1300537 (Apr. 6, 2007).

Office action from U.S. Appl. No. 10/436,376, mailed Apr. 19, 2007.
Office action from U.S. Appl. No. 10/436,376, mailed Aug. 24, 2006.
Office action from U.S. Appl. No. 10/436,376, mailed Feb. 14, 2006.
Notice of Allowance from U.S. Appl. No. 10/436,376, mailed Apr. 1, 2005.
Office action from U.S. Appl. No. 10/436,376, mailed Dec. 1, 2004.

Ward, Edmund W.B., The Interactionof Soya Beans with *Phytophthora megasprema* f.sp. glycinea: Pathogenicity, Biological Control of Soil-borne Plant Pathogens, edited by D. Homby, 1990, pp. 311-327.

* cited by examiner

IDENTIFICATION OF SOYBEANS HAVING RESISTANCE TO *PHYTOPHTHORA SOJAE*

CROSS REFERENCE TO RELATED APPLICATIONS

This application is a continuation in part of U.S. Ser. No. 10/436,376, filed May 12, 2003, which claims priority to U.S. Provisional Application No. 60/379,304, filed May 10, 2002, and U.S. Provisional Application No. 60/427,637, filed Nov. 19, 2002, all of which are incorporated herein by reference in their entirety.

STATEMENT ON GOVERNMENT FUNDED RESEARCH

The present invention was made, at least in part, with support from the United States Department of Agriculture through Hatch Fund grants made to the Ohio Agricultural Research and Development Center. The United States Government has certain rights in the invention.

BACKGROUND OF THE INVENTION

This invention relates to soybean plants possessing a novel resistance to *Phytophthora sojae*, which maps to a chromosomal locus and methods for identifying and breeding these plants, the methods involving marker assisted selection.

Soybeans, (*Glycine max* L. Merr) are a major cash crop and investment commodity in North America and elsewhere. Soybean oil is one of the most widely used edible oils, and soybeans are used worldwide both in animal feed and in human food production. *Phytophthora* root and stem rot is a devastating disease of soybean that occurs throughout the U.S. and the world (Wrather et al., Can. J. Plant Pathol., 2001). *Phytophthora* root and stem rot caused by *Phytophthora sojae* is the second leading cause of yield loss in soybean in the United States. Yield losses in 1998, due to *Phytophthora* root and stem rot in top soybean producing countries were 1149 and 92 thousand metric tons in the U.S. and Argentina, respectively (Wrather et al., Can. J. Plant Pathol., 2001). General resistance mechanisms against *P. sojae* include structural features of the host, preformed chemical inhibitors, induced structural barriers, hypersensitive reactions and phytoalexins (Erwin et al., eds, *Phytophthora*, 1983). *Phytophthora* root and stem rot was first described in Ohio and shortly thereafter it was described in Indiana and North Carolina (Suhovecky and Schmittthenner, 1955). The pathogen is now referred to as *Phytophthora sojae*.

Resistance to *Phytophthora* root and stem rot is a trait provided by multiple alleles. To date, thirteen resistance (Rps) alleles at seven loci have been described; Rps1 (Bernard et al., Agron. J., 1957), Rps2 (Kilen et al., Crop Sci., 1974), Rps3 (Mueller, Phytopathology, 1978), Rps4 (Athow et al., Phytopathology, 1980), Rps5 (Buzzell and Anderson, Soybean Genet. Newslett., 1981), Rps6 (Athow and Laviolette, Phytopathology, 1982), and Rps7 (Anderson and Buzzel, Plant Dis., 1992). The Rps resistance loci are found on soybean major linkage groups (MLGs) N, J, F, and G (Demirbas et al., Crop Science, 2001; Diers et al., Crop Science, 1992). Populations of *P. sojae* exist in many soybean production regions that cause disease on plants with many, if not all, of these Rps genes.

Single gene resistance has provided adequate disease management; however, each single gene deployed in a soybean cultivar is only effective for eight to fifteen years (Schmitthenner, Plant Dis., 1985). Pathotypes of *P. sojae*, containing virulence genes to Rps1k (the most recently deployed Rps gene) have already been found in fields throughout the midwest (Abney et al., 1997; Dorrance et al., 2003, Kaitany et al., 2001; Kurle and ElAraby, 2001; Leitz et al, 2001; Schmitthenner et al., 1994; Tang et al., 1996). Accordingly, novel resistance loci or alleles are desirable for introduction into commercial soybean lines to protect against yield losses caused by *P. sojae*.

SUMMARY

A novel method is provided for determining the presence or absence of *Phytophthora* resistance in a soybean plant, soybean seed, or soybean germplasm, as indicated by the presence or absence of a newly-discovered resistance gene, which maps to linkage group MLG F (referred to hereinafter as Rps8). The Rps8 locus comprises a gene associated with resistance to *Phytophthora sojae*. The Rps8 gene is capable of conveying *Phytophthora sojae* resistance to susceptible soybean germplasm. In accordance with the present invention, the Rps8 gene is mapped to MLG F by genetic markers Satt595, Satt114, Satt334, Sat_317, Sat_197, Satt510, Satt335 and Satt144, and the Rps8 gene is located along the trait locus between the markers. According to the method, genomic DNA from a soybean plant, soybean seed, or soybean germplasm is analyzed for the presence of the Rps8 gene. The presence of the Rps8 gene is determined through the use of one or more molecular markers linked to Rps8. According to the method, molecular information regarding the Rps8 gene may be used to aid in the selection of breeding plants, lines, and populations containing *Phytophthora* resistance for use in introgression of this trait into elite soybean germplasm, or germplasm of proven genetic superiority suitable for variety release. Also according to the method, molecular information regarding the Rps8 gene may be used to confirm selection of *Phytophthora* resistance in new soybean cultivars.

Also provided is a method for introgressing soybean *Phytophthora sojae* resistance gene Rps8 into susceptible soybean germplasms. According to the method, nucleic acid markers linked to Rps8 are used to select soybean plants containing the Rps8 gene. Plants so selected have a high probability of expression of *P. sojae* resistance. Plants so selected can be used in a soybean breeding program. Through the process of introgression, the Rps8 gene is introduced from plants identified via marker assisted selection to other plants. According to the method, agronomically desirable plants and seeds can be produced containing the gene for Rps8 from germplasm containing Rps8. One particular example of the source of Rps8 resistance is the OX-99128 population, or a descendant of this population. Similarly, the source of *Phytophthora sojae* resistance may conveniently include the OX-98317 population, or a descendant of this population.

Also provided is a method for producing an inbred soybean plant adapted for conferring, in hybrid combination with a suitable second inbred, Rps8-derived resistance to *Phytophthora sojae*. First, donor soybean plants containing Rps8 are selected. According to the method, selection is accomplished via nucleic acid marker assisted selection, as previously explained. Selected plant material may represent, among others, an inbred line, a hybrid, a heterogeneous population of soybean plants, or simply an individual plant. According to techniques well known in the art of plant breeding, this Rps8-donor parental line is crossed with a second parental line. Preferably, the second parental line is high yielding. This cross produces a segregating plant population composed of genetically heterogeneous plants. Plants of the segregating plant population are screened for the locus Rps8. Those plants having Rps8 are selected for further breeding until a line is obtained which is homozygous for resistance to *Phytophthora sojae* at Rps8. This further breeding may include, among other techniques, additional crosses with other lines, hybrids, backcrossing, or self-crossing. The result is an inbred line of soybean plants that are resistant to *Phytophthora sojae* in combination with other desirable traits from one or more other inbred lines.

Also provided is soybean germplasm designated HFX01-602 (also referred to as OX-01602). The parental lineage for HFX01-602 is shown in FIG. 2. This seed has ATCC accession number PTA-5190. HFX01-602 was produced by introgressing an Rps8 gene from a germplasm having Rps8-derived *P. sojae* resistance into non-resistant or less resistant soybean germplasm. The invention includes all HFX01-602 progeny that contain the locus Rps8 and exhibit *Phytophthora sojae* resistance. Also provided are populations of soybean plants, seed, tissue cultures, variants, and mutants that are produced from HFX01-602 Rps8-containing germplasm.

Also provided is soybean germplasm designated OX-98317. OX-98317 was produced by introgressing disease resistance, identified via Rps8, a novel locus for *Phytophthora sojae* resistance originally found in Korean PI399073, into non-resistant or less resistant soybean germplasm. The germplasm includes all OX-98317 progeny that contain the locus Rps8 and exhibit *Phytophthora sojae* resistance. Also provided are populations of soybean plants, seed, tissue cultures, variants, and mutants that are produced from OX-98317 Rps8-containing germplasm.

Also provided is soybean germplasm designated OX-99218. OX-99218 was produced by introgressing disease resistance, identified via Rps8, a novel locus for *Phytophthora sojae* resistance originally found in Korean PI399073, into non-resistant or less resistant soybean germplasm. The germplasm includes all OX-99218 progeny that contain the locus Rps8 and exhibit *Phytophthora sojae* resistance. Also provided are populations of soybean plants, seed, tissue cultures, variants, and mutants that are produced from OX-98218 Rps8-containing germplasm.

Also provided is soybean germplasm designated OX-99128. OX-99128 was produced by introgressing disease resistance, identified via Rps8, a novel locus for *Phytophthora sojae* resistance originally found in Korean PI1 399073, into non-resistant or less resistant soybean germplasm. The germplasm includes all OX-99128 progeny that contain the locus Rps8 and exhibit *Phytophthora sojae* resistance. Also provided are populations of soybean plants, seed, tissue cultures, variants, and mutants that are produced from OX-99128 Rps8-containing germplasm.

DETAILED DESCRIPTION

Definitions

Figure 1:
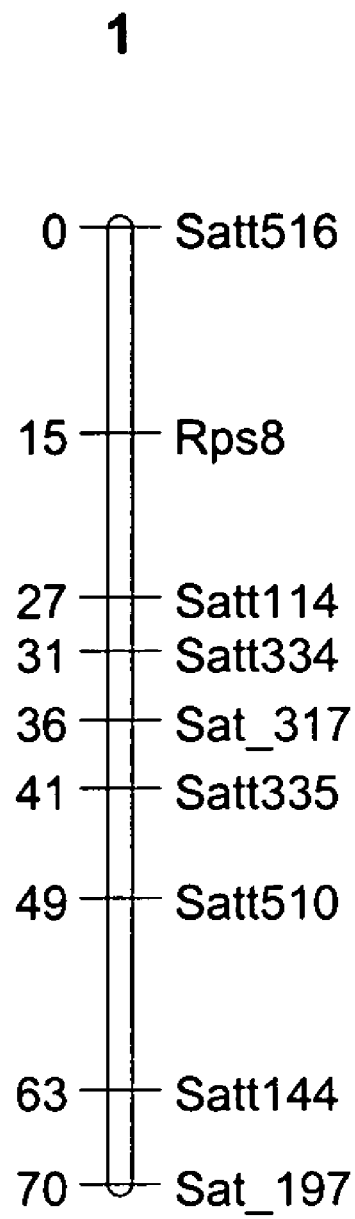
FIG. 1 shows a genetic linkage map of MLG F of soybean. The genetic linkage map was constructed using Joinmap 3.0 linkage analysis software with molecular marker data (Van Ooijen and Voorrips, 2001). Distances between markers were assigned in centimorgans, shown to the left of the chromosome. Simple Sequence Repeat (SSR) markers and Rps8 are shown to the right of the chromosome. The determination of linkage groups was done with a log-likelihood (LOD) threshold of 3.0. The calculation of linkage maps was performed using all pairwise recombination estimates smaller than 0.45 and a LOD score larger than 0.05. Kosambi's mapping function was used.

"Allele" is any of one or more alternative forms of a gene, all of which alleles relate to one trait or characteristic. In a diploid cell or organism, the two alleles of a given gene occupy corresponding loci on a pair of homologous chromosomes.

"Backcrossing" is a process through which a breeder repeatedly crosses hybrid progeny back to one of the parents, for example, a first generation hybrid $F_1$ with one of the parental genotypes of the $F_1$ hybrid.

"Cultivar" and "variety" are used synonymously and mean a group of plants within a species (e.g., *Glycine max*) which share certain constant characters that separate them from the typical form and from other possible varieties within that species. While possessing at least one distinctive trait, a variety is also characterized by a substantial amount of overall variation between individuals within the variety, based primarily on the Mendelian segregation of traits among the progeny of succeeding generations.

"Gene" means a specific sequence of nucleotides in DNA that is located in the germplasm, usually on a chromosome, and that is the functional unit of inheritance controlling the transmission and expression of one or more traits by specifying the structure of a particular polypeptide or controlling the function of other genetic material.

"Germplasm" means the genetic material with its specific molecular and chemical makeup that comprises the physical foundation of the hereditary qualities of an organism. As used herein, germplasm includes living tissue from which new plants may be grown; or, another plant part, such as leaf, stem, pollen, or cells, that may be cultured into a whole plant.

"Hybrid plant" means a plant offspring produced by crossing two genetically dissimilar parent plants.

"Inbred plant" means a member of an inbred plant strain that has been highly inbred so that all members of the strain are genetically identical, with the exception of sexual differences.

"Introgression" means the entry or introduction by hybridization of a gene or trait locus from the genome of one plant into the genome of another plant that lacks such gene or trait locus.

"Line" or "strain," as distinguished from a "variety," means a group of plants which display less variation between individuals, generally (although not exclusively) by virtue of several generations of self-pollination, and includes a group of plants which carry a gene or locus for a particular trait, specifically the Rps8-derived *Phytophthora sojae* resistance trait as disclosed herein.

"Linkage group" means an identified chromosomal region containing genetic material that expresses a desired trait.

"Locus" means a chromosomal region where a polymorphic nucleic acid or trait determinant or gene is located.

"Polymorphism" means a change or difference between two related nucleic acids. A "nucleotide polymorphism" refers to a nucleotide which is different in one sequence when compared to a related sequence when the two nucleic acids are aligned for maximal correspondence. A "genetic nucleotide polymorphism" refers to a nucleotide which is different in one sequence when compared to a related sequence when the two nucleic acids are aligned for maximal correspondence, where the two nucleic acids are genetically related, i.e., homologous, e.g., where the nucleic acids are isolated from different strains of a soybean plant, or from different alleles of a single strain, or the like.

"Marker assisted selection" means the process of selecting a desired trait or desired traits in a plant or plants by detecting one or more nucleic acids from the plant, where the nucleic acid is associated with the desired trait.

"Plant" means plant cells, plant protoplast, plant cell or tissue culture from which soybean plants can be regenerated, plant calli, plant clumps and plant cells that are intact in plants or parts of plants, such as seeds, pods, flowers, cotyledons, leaves, stems, buds, roots, root tips and the like.

"Probe" means an oligonucleotide or short fragment of DNA designed to be sufficiently complementary to a sequence in a denatured nucleic acid to be probed and to be bound under selected stringency conditions.

"Qualitative trait" means a trait which is controlled by a single dominant gene and which segregates according to normal Mendelian genetic principles.

"Rps8-derived resistance" means P. sojae resistance in a soy germplasm that is provided by the heterozygous or homozygous expression of the gene within the Rps8 locus mapped to MLG F "Rps8 phenotype" means resistance to P. sojae by soybean germplasm, as demonstrated by resistance to P. sojae after inoculation with same according to the methods described herein.

"Rps8 soybean plant" means a plant having resistance to P. sojae that is derived from the presence and expression of at least one Rps8 gene, or that is shown to have an Rps8 gene at the Rps8 locus described herein.

"Self-crossing" is a process through which a breeder crosses hybrid progeny with one another, for example, a second generation hybrid $F_2$ with itself to yield progeny designated $F_{2:3}$.

As used herein, the terms "segregate," "segregants," "co-segregate," "hybrid," "crossing," and "selfing" refer to their conventional meanings as understood in the art (see, for instance, Briggs, F. N. and Knowles, P. F. and, Introduction to Plant Breeding (Reinhold Publication Corp., New York, N.Y., 1967).

Rps8 Gene and Rps8-derived P. sojae Resistance

The plant introduction PI 399.073 is the only known soybean cultivar to have Rps8-derived resistance to *Phytophthora sojae*. However, PI 399.073 has poor agronomic traits, necessitating the introgression of its Rps8-derived resistance into other soybean germplasms having more desirable traits. Conventional breeding with PI 399.073, as described below, produced several germplasms which are more agronomically desirable and can be used as a source of Rps8-derived *Phytophthora sojae* resistance in future soybean breeding.

The locus of the Rps8 gene has been mapped according to the methods provided herein using nucleic acid markers, and is further defined by the association of Rps8 with particular recognized linkage groups. Rps8 is located on major linkage group (MLG) F of the soybean map (See Figure One). Rps8 is identified and localized using traditional crossing populations and disease assays combined with simple sequence repeat (SSR) molecular markers Satt595, Satt114, Satt334, Sat_317, Sat_197, Satt510, Satt335 and Satt144.

Identification of *Phytophthora sojae* Resistance Trait Loci

It is of particular importance both to the soybean breeder and to farmers who grow and sell soybeans as a cash crop to identify the trait loci for resistance to the various pathotypes of *Phytophthora sojae*. With information about such trait loci, soybean breeders are better equipped to breed *Phytophthora* resistant soybeans which are agronomically desirable (i.e., they also possess other genotypic and phenotypic characteristics required for commercial soybean lines).

Soybean germplasm from plant introductions (PIs) from South Korea serve as potential new sources of resistance loci (Dorrance and Schmitthenner, 2000). Soybean germplasm from South Korea has previously been the source of Rps alleles, such as Rps3a from PI86972-1 (Mueller et al., 1978). Although these South Korean plant introductions are generally considered agronomically poor, some of the alleles that they carry are valuable and can be moved into more suitable backgrounds for U.S. cultivars through selective breeding techniques, in particular the breeding procedure known as introgression.

Soybean Breeding and Selection Methods

Soybean varieties possessing specific, desirable traits may be developed by traditional plant breeding techniques. Two cultivars or germplasms are typically selected for particular traits and then interbred, one being employed as male and the other as female. After the first cross, the $F_2$ generation plants are normally screened for the traits of interest. Seeds are saved from the $F_2$ plants selected and subsequent generations are grown up, again selecting desirable plants from each generation.

The desired phenotype of the novel Rps8 gene is transferred to other wild-type or commercial soybean germplasms by conventional plant breeding methods to achieve a new germplasm line combining these desired phenotypes with other valuable agronomic traits such as, for example, seed size, protein content, and herbicide resistance. The desired wild-type soybean, commercial cultivar, or hybrid thereof is crossed by conventional plant breeding methods with a soybean plant having the Rps8 gene and phenotype. Breeding methods used in accordance with the present invention include, for example, methods described in Knowles, P. F. and F. N. Briggs, Introduction to Plant Breeding (Reinhold Publication Corp., New York, N.Y., 1967), incorporated herein by reference, or any like methods known in the art. Hybrid progeny exhibiting the Rps8 phenotype are selected.

The Rps8 phenotype is controlled by a single dominant gene, which segregates according to normal Mendelian genetic principles. Conventional plant breeding techniques can therefore be used to introduce the phenotype into any soybean variety. Thus, by conventional plant breeding techniques, the ordinary artisan can cross an Rps8 soybean plant with any other soybean germplasm having specific desirable traits to produce a soybean line possessing the combination of desired phenotypes. The present invention is exemplified by its application to soybean (*Glycine max*); however, its operating principles may be applied to other species of soybean. The invention is not limited to any particular soybean cultivar, but may be applied generally to any plant variety of the genus *Glycine*, whether wild, domestic or hybrids of the two. Although the instant invention is applicable to all soybean varieties, the breeding and selection methods are preferably carried out by crossing soybean lines which contain the Rps8 gene with varieties possessing other valuable agronomic traits. Soybean varieties are widely available in commerce from several manufacturers, providing progenitor strains having a broad range of agronomically desirable traits.

Introgression

Selective breeding techniques for introgressing one or more desired traits from one soybean plant line into another plant line having other desired traits have several advantages over modern genetic engineering techniques. While a great deal of emphasis is usually placed on the strategy of introducing characteristics into plants via genetic engineering techniques, the prospects for the general use of these techniques for plant improvement are greatly limited by the realization that very few genes corresponding to plant traits of interest have been identified. The use of direct gene transfer in manipulating these traits is therefore difficult due to problems in pinpointing and then cloning those individual loci which contribute predominantly to the expression of the trait.

The introgression of traits from one germplasm to another conventionally involves the identification of germplasms having favorable genotypes in a segregating generation followed by repeated backcrossing to commercially acceptable cultivars. This procedure is feasible for simply inherited qualitative traits, when one or only a few genes control a trait. As the number of genes controlling a trait increases, screening the number of F2 segregants required to identify at least one individual which represents the ideal (homozygous) genotype quickly becomes prohibitive. For example, with one gene and two alleles of equal frequency, the probability of recovering a desirable genotype on the F2 generation is 1/4. However, if the number of genes is increased to 5 or 10, the probability of recovering an ideal genotype in the F2 population is reduced to approximately one in one thousand and one in one million, respectively. Thus, to identify desirable segregants, one must either reduce the number of segregants needed or have available very efficient screening procedures. Marker assisted selection is an efficient screening procedure for expediting introgression, whether there is a single or multiple genes that define a desired trait.

Identification and Selection Based on Markers

The ability to characterize an organism, such as a soybean plant, by its genome is possible because of the inherent variability of genetic information. Although DNA sequences which code for necessary proteins are well conserved across a species, there are regions of DNA which are non-coding or code for portions of proteins which do not have critical functions and therefore, absolute conservation of nucleic acid sequence is not strongly selected for. These variable regions are identified by genetic markers.

Genetic markers can be detected by amplification of specific DNA sequences or amplicons which correspond to unique regions of the genome. Use of sequence-specific PCR primers allows confirmation of either or both the presence or location of a DNA sequence in the genome of the subject being tested. Polymorphisms which are represented by unique and different sequences are most useful as markers because they permit discrimination using a variety of genotyping procedures, as set forth herein. Various genetic markers include, but are not limited to, markers based on protein sequence, isozymes; hybridization, restriction fragment length polymorphisms ("RFLP"); and polymerase chain reaction, single sequence repeats ("SSR,") or microsattelites, or short tandem repeats, random amplified polymorphic DNA ("RAPD") and amplified fragment length poymorphisms (AFLPs).

Through the combination of introgression and indirect selection procedures, plant breeders are able to increase efficiency in the testing of traits which are difficult or expensive to evaluate. Genetic markers closely linked to important genes may be used to indirectly select for favorable alleles more efficiently than direct phenotypic selection (Lande and Thompson, Genetics 124:543-546, 1990). In the past, numerous inoculations with different pathotypes of *P. sojae* were needed to confirm the presence of a new resistance allele in a number of soybean crosses. Mapping new alleles was also difficult due to the limited number of classical gene markers. DNA marker technology, especially SSR, has eliminated the need for numerous pathotype inoculation screenings and has expedited the process of mapping a new gene with more precision.

Using marker assisted selection, a DNA sample from soybean plants is required. The sample is amplified using conventional techniques to provide a set of differentially amplified nucleic acids in the mixture. At least one of the differentially amplified nucleic acids is mapped to a unique genetic polymorphism, thereby providing a marker for the polymorphism. Typically, more than one differentially amplified nucleic acid is mapped, thereby providing a set of markers. The set can be of any size, although more information is provided by larger sets. Typical set sizes are from about 1-100 markers, generally about 1-5 markers. In one approach, the method includes hybridizing a probe nucleic acid to a mixture of DNA amplified from a biological source of DNA comprising the polymorphism, thereby identifying the polymorphism in the biological source of DNA. The probe nucleic acid is hybridized under stringent conditions to a target nucleic acid comprising the polymorphism.

Marker assisted selection involves crossing a parent plant having a desired allelic trait, for example, *P. sojae* resistance, with a second parent plant in order to create an F1 plant population. Heterozygous plants from the F1 population are self-fertilized, or "selfed," to create a segregating F2 plant population exhibiting expression of the qualitative trait of interest, e.g., *P. sojae* resistance. Following preparation a marker (such as SSR, RFLP, RAPD, or isozyme) is randomly chosen, or alternatively, selected from a genetic linkage map, and evaluated on the population. Using other markers, the degree of association between the trait of interest and each particular marker is determined. In this manner, the marker(s) having the strongest association with the trait of interest can be determined and utilized, for example, in a breeding program to select plants having *P. sojae* resistance. One or a combination of markers can be used to identify or confirm the presence of an associated trait locus, such as Rps8. Combinations of markers, such as at least two markers that are known by mapping to bracket or flank the trait locus of interest can be used effectively to identify or confirm the presence of the trait locus in hybrid introgressed germplasms. Particularly where one or more markers are not strongly associated with the trait of interest, use of multiple, and particularly flanking markers, will increase the probability of positively confirming the isolation or presence of the trait locus of interest.

Probes, Techniques and Conditions for Molecular Marker Analysis

Probes for use in marker assisted selection can be acquired commercially or can be made using known sequence information or information acquired by providing first and second samples of amplified DNA, comparing the first and second samples of amplified DNA to identify differentially amplified DNAs. The differentially amplified DNA can be isolated and mapped. Typically, at least a portion of the genetically mapped isolated DNA is sequenced to identify associated polymorphisms. Oligonucleotide probes can then be prepared comprising a portion of the sequenced region. Preferred probes uniquely map to single sites in a haploid genomic DNA of a plant or animal, or to cDNA. Many probes are commercially available for use in marker assisted selection using a broad range of known markers.

A labeled probe is exposed to amplified mixtures of DNA in a biological sample and is assessed for binding. For example, a marker comprising a polymorphic nucleic acid can be detected by allele-specific hybridization of a probe to the region of the marker comprising the polymorphic nucleic acid. Similarly, a marker can be detected by Southern analysis, northern analysis, in situ analysis, or the like.

Hybridization of probes to amplified mixtures of DNA (e.g., DNA amplified by AFLP techniques) is a preferred assay format. "Hybridization" is used to denote the pairing of complementary nucleotide sequences to produce a DNA-DNA hybrid a DNA-RNA hybrid or an RNA-RNA hybrid. Complementary base sequences are those sequences that are related by the well-known base-pairing rules. In DNA, A pairs with T, and C pairs with G. In RNA, U pairs with A, and C pairs with G. Two single-stranded nucleic acids "hybridize" when they form a double-stranded duplex. The region of double-strandedness can include the full-length of one or both of the single-stranded nucleic acids, or all of one single stranded nucleic acid and a subsequence of the other single stranded nucleic acid, or the region of double-strandedness can include a subsequence of each nucleic acid.

"Stringent hybridization conditions" in the context of nucleic acid hybridization are sequence dependent and are different under different environmental parameters. An extensive guide to the hybridization of nucleic acids is found in Tijssen (1993) Laboratory Techniques in Biochemistry and Molecular Biology-Hybridization with Nucleic Acid Probes, part I chapter 2, "Overview of principles of hybridization and the strategy of nucleic acid probe assays" Elsevier, New York. Generally, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Highly stringent conditions are selected to be equal to the $T_m$ point for a particular probe. Sometimes the term "$T_d$" is used to define the temperature at which at least half of the probe dissociates from a perfectly matched target nucleic acid. In any case, a variety of estimation techniques for estimating the $T_m$ or $T_d$ are available, and generally described in Tijssen, id. Typically, G-C base pairs in a duplex are estimated to contribute about 3° C. to the $T_m$, while A-T base pairs are estimated to contribute about 2° C., up to a theoretical maximum of about 80-100° C. However, more sophisticated models of $T_m$ and $T_d$ are available and appropriate in which G-C stacking interactions, solvent effects, the desired assay temperature and the like are taken into account.

An example of stringent hybridization conditions for hybridization of complementary nucleic acids that have more than 100 complementary residues on a filter in a Southern or northern blot is 50% formalin with 1 mg of heparin at 42° C., with the hybridization being carried out overnight. An example of stringent wash conditions for a Southern blot of such nucleic acids is a 0.2 times SSC wash at 65° C. for 15 minutes (see, Sambrook, supra for a description of SSC buffer). Often the high stringency wash is preceded by a low stringency wash to remove background probe signal. An example low stringency wash is 2 times SSC at 40° C. for 15 minutes.

Introgressed Soybean Lines Having Rps8-derived *P. Sojae* Resistance: Description of HFX01-602 Soybean Germplasm with Rps8 Resistance to *Phytophthora sojae*

HFX01-602 (also referred to as OX01-602) germplasm was developed as an $F_{3:4}$ population from the cross of Kottman x OX-99393. OX-99393 is from the cross OX-98317 x Kottman. OX-98317 is from the cross PI 399.073 x NK S19-90. Crosses were made without selection. S 19-90 carries the Rps1c resistance gene. Kottman was developed at the Ohio Agricultural Research and Development Center as an F4-derived line from the cross HS88-7363 x HS88-4988. The female parent HS88-7363 is the F2-derived line from which 'General' was selected and derives from Voris '311' x 'Resnik'. The male parent, HS88-4988, is from 'Winchester' x A83-271027. The line A83-271027 is from Northrup King 'S1492' x Asgrow 'A3127'. Kottman is an indeterminate cultivar of maturity group III with white flowers, light tawny pubescence, and tan pods. Seeds are dull yellow with black hila. Kottman has both the Rps1k and the Rps3 genes for resistance to *Phytophthora* rot. Kottman is susceptible to brown stem rot, soybean cyst nematode, and *sclerotinia* white mold. In Ohio tests, seeds of Kottman had a mean content of 43.2% protein and 20.1% oil, in comparison with 43.3% protein and 19.9% oil for General. Kottman was released because of its high yield in relation to cultivars of similar maturity and its resistance to *Phytophthora* rot. OX-99393 and HFX01-602 have the novel resistance locus containing Rps8 derived from Korean PI 399073.

The HFX01-602 germplasm includes seeds. 2500 HFX01-602 $F_{2:3}$ seeds were deposited with the American Type Culture Collection. The population of seeds was obtained from bulking the seeds produced by $F_2$ progeny. The genotype of the seed population is approximately 25% Rps8/Rps8, approximately 50% e Rps8/sus, and approximately 25% sus/sus.

Description of OX-99218 Soybean Germplasm with Rps8 Resistance to *Phytophthora sojae*

OX-99218 was developed as an $F_1$ derived population of bulk $F_4$ seed from the cross of A97-873014 x OX-98317. OX-98317 was developed from the cross of Korean PI 399073 x S19-90. S 19-90 carries the Rps1c resistance gene. A97-873014 does not have any known *Phytophthora* resistance genes. OX-98317 has the novel resistance gene Rps8 derived from Korean PI 399073. The F1 (hybrid) plant was produced by crossing, while the next three generations were produced by self crossing. "F1-derived" indicates that there was no further selection of single plants after the F1 generation. That is, the F2 seeds were collected from the original F1 (hybrid) plant. These were planted and the whole plot was harvested in bulk to give F3 seeds. A portion of these seeds was then planted and again harvested to provide the F4 seeds. Soybean is naturally self-fertilized, so each plant from the F1 onward produced its own seeds by self crossing.

Table 1 provides OX-99218 Phenotypic Data. Plants were inoculated with pathotype OH30 (vir 1a, 1b, 1k, 2, 3a, 4, 5, 6, 7) to test for segregation of a single resistance gene, "Rps8." Plants were also inoculated with pathotype OH4 (vir 1a, 1c, 7) to determine if the Rps1c was still present from the S19-90. Similar segregation ratios for Race 30 and Race 4 indicate only Rps8 was present.

TABLE 1

| Cross | Patho-type | Resistant or segregating plants | Susceptible plants | Test ratio | χ2 prob-ability |
|---|---|---|---|---|---|
| A97-873014 x OX-98317 | OH30 | 15 | 17 | 9:7 | 0.5-0.25 |
| A97-873014 x OX-98317 | OH4 | 7 | 12 | 9:7 | 0.1-0.05 |

Table 2 provides OX-99218 Genotypic Data—Plants inoculated with OH30 were tested with a molecular marker linked to the "Rps8".

TABLE 2

| Cross | Resistant plants | Segregating Plants | Susceptible plants | Test ratio | χ2 probability |
|---|---|---|---|---|---|
| A97-873014 × OX-98317 | 10 | 5 | 17 | 7:2:7 | 0.05-0.025 |

Description of OX-99128 Soybean Germplasm with Rps8 Resistance to *Phytophthora sojae*

OX-99128 was developed as an $F_1$ derived population of bulk $F_4$ seed from the cross of Darby X OX-98317. OX-98317 was developed from the cross Korean PI 399073 x S19-90. S 19-90 carries the Rps1c resistance gene. Darby contains the resistance gene Rps1k. OX-98317 has the novel Rps8 resistance locus derived from PI399073. A pathotype of *Phytophthora sojae* that has a susceptible interaction with Rps1k was used to inoculate plants from this cross in order to observe only the effect of "Rps8".

Table 3 provides OX-99128 Phenotypic Data—Plants were inoculated with pathotype OH30 (vir 1a, 1b, 1k, 2, 3a, 4, 5, 6, 7) to test for segregation of a single resistance gene. Plants were also inoculated with pathotype OH4 (vir 1a, 1c, 7).

TABLE 3

| Cross | Pathotype | Resistant or segregating plants | Susceptible plants | Test ratio | χ2 probability |
|---|---|---|---|---|---|
| Darby X OX-98317 | OH30 | 12 | 19 | 9:7 | 0.05-0.025 |
| Darby X OX-98317 | OH4 | 20 | 0 | 13:3 | 0.05-0.025 |

Table 4 provides OX-99128 Genotypic Data—Plants inoculated with OH30 were tested with a molecular marker linked to the "Rps8".

TABLE 4

| Cross | Resistant plants | Segregating Plants | Susceptible plants | Test ratio | χ2 probability |
|---|---|---|---|---|---|
| Darby × OX-98317 | 8 | 4 | 17 | 7:2:7 | 0.25-0.10 |

Germplasm Deposit Information

A deposit of 2500 viable seeds of the inbred soybean germplasm designated HFX01-602 has been made with the American Type Culture Collection ("ATCC"), 10801 University Blvd., Manassas, Va. on May 9, 2003. Those deposited seeds have been assigned ATCC Accession No. PTA-5190. The deposit was made in accordance with the terms and provisions of the Budapest Treaty. All restrictions on the availability to the public of the materials so deposited will be irrevocably removed upon the granting of the patent. The germplasm will be maintained for a term of at least thirty (30) years and at least five (5) years after the most recent request for the furnishing of a sample of the deposit is received by the depository, and at least beyond the enforceable life of the patent(s) for which the deposit was made, whichever is longer. The germplasm will be replaced if it becomes nonviable during that period. Additionally, the deposit has satisfied all the requirements of 37 C.F.R. §§ 1.801-1.809, including a mechanism for providing an indication of the viability of the sample. The deposit does not constitute a waiver of any rights that may be granted under this or any other patent application or under the Plant Variety Protection Act (7 U.S.C. 2321), or any other applicable treaty, law or regulation. This deposit was made to further exemplify the invention and is not intended to any way limit the scope of the invention.

EXAMPLES

Example 1

Phenotypic Evaluation of Rps8-derived *Phytophthora sojae* Resistance

Korean plant introductions (PI399073) were obtained from the USDA Soybean Germplasm Collection in Urbana, Ill. All other plant material was obtained from the Ohio Agricultural Research Development Center (OARDC) soybean breeding program. The crosses used for mapping the new Rps8 allele were Williams (rps) X PI399073, S 19-90 (Rps1c) X PI399073, and Williams (rps) X PI399073. The $F_1$ plants from these crosses were selfed to produce populations of approximately 40 to 60 and 143 $F_2$ plants for each cross. The $F_2$ plants were then selfed and each plant was thrashed individually to yield seed for $F_{2:3}$ families.

Isolates of *P. sojae* pathotypes were maintained at the Department of Plant Pathology, OARDC. All pathotypes used in this study were collected in Ohio. Three isolates of *P. sojae* were used in this study with the following pathotypes OH1 (vir 7), OH17 (vir 1b, 1d, 3a, 3b, 3c, 4, 5, 6, 7), and OH25 (vir 1a, 1b, 1c, 1k, 7). Differential checks, Williams (universal suscept); Harlon (Rps1a), Harosoy 13XX (Rps1b), Williams 79 (Rps1c); PI1103091 (Rps1d); Williams 82 (Rps1k); L76-1988 (Rps2); L83-570 (Rps3); PRX 146-36 (Rps3b); PRX 145-48 (Rps3c); L85-2352 (Rps4); L85-3059 (Rps5); Harosoy 62XX (Rps6) and Harosoy (Rps7), were included in all tests to ensure that the *P. sojae* isolate used elicited the appropriate reaction.

Ten individual F3 seedlings per F2:3 family were inoculated in the laboratory using a modification of the hypocotyl inoculation technique. Inoculum was prepared by growing the *P. sojae* isolates for one week on lima bean agar (50 g lima beans, 12 g agar per liter). Seeds were placed between germination papers wetted with water, rolled up, and stored in the dark in plastic containers. The plastic containers had wire mesh in the bottom to allow for water to drain from the papers. After one week of growth, papers were unrolled and the seedlings were inoculated using a hypodermic syringe. The syringe was filled with colonized agar from a plate of *P. sojae*, and then the agar was forced through the syringe to create a slurry. The slurry was placed back into the syringe. Seedlings were inoculated by scratching the hypocotyl with the needle of the hypodermic syringe and placing the agar/mycelium mixture onto the wound. Reactions were recorded as R (resistant; seedlings alive) or S (susceptible, seedlings dead with brown hypocotyls) after 10 days. Each F2:3 family had 10 to 25 plants scored, either all R, all S, or a combination of both. The 10 scores were used to develop a single classification, R, S, or H (heterogeneous), for each F2 plant from which an F2:3 was derived.

Chi-square analyses were performed on the phenotypic data to test if a 3:1 resistant to susceptible ratio was present. F2 plants were scored as R, S, or H based on the results of the hypocotyl inoculation of the F2:3 families. For this analysis all R and H scores were grouped together.

The cross of Williams X PI399073 resulted in F2:3 families that fit a 3:1 resistant to susceptible phenotypic ratio in both populations. Forty-five individual F3 seedlings from 143 F2:3 families were inoculated with *P. sojae* pathotype vir 7 (OH-race 1) and after 10 days 109 F2:F3 families were scored as resistant and 34 were scored as susceptible ($\chi2=0.9$) (Table 5). In order to confirm this result, 15 additional F3 seedlings from each F2 plant were inoculated with pathotype Race 25. A 3:1 ratio was observed again using this second pathotype, and the same F2:3 families were susceptible in both tests.

Table 5 provides a summary of phenotypic ratios of 143 F2:3 families tested with different pathotypes of *P. sojae* from the Williams X PI399073 cross.

TABLE 5

| Cross | Patho-type | Resistant or Segregating Lines | Susceptible Lines | Test Ratio | $\chi2$ value | $\chi2$ probability |
|---|---|---|---|---|---|---|
| Williams X PI399073 | OH1 (vir 7) | 109 | 34 | 3:1 | 0.9 | 0.75–0.50 |

Example 2

Simple Sequence Repeat (SSR) DNA Length Polymorphism Markers Indicating Association of SSR markers Satt595, Satt114, Satt334, Sat_317, Sat 197, Satt510, Satt335 and Satt144 with *Phytophthora sojae* Resistance in PI399073, thus Placing the Novel Trait Locus for Rps8 on Major Linkage Group (MLG) F.

The cross used for analyzing SSR marker association was Williams (Rps) X PI 399073. The $F_1$ plants from this cross were selfed to produce a population of approximately 150 $F_2$ plants. The $F_2$ plants were then selfed and each plant was thrashed individually to yield seed for $F_{2:3}$ families.

Whole plants from individual F3 seedlings were bulked from each F2:3 family, and DNA was extracted as previously described (Saghai-Maroof et al., 1984). SSR primer pairs (Research Genetics Inc., Huntsville, Ala.), polymorphic for the parents in each cross, were used to test the F2:3 progeny. PCR reactions were performed as recommended by the manufacturers in a total of 20 µl containing 30 ng of genomic DNA. Amplified PCR products were resolved on 5% high-resolution agarose gels (Amresco, Solon, Ohio) and stained with ethidium bromide for visualization of the DNA products. Reactions were scored as 2 (homozygous for PI parent allele), 1 (homozygous for susceptible parent allele), or 3 (heterozygous).

Thirty-eight SSR markers were polymorphic between Williams and PI399073. These markers were then tested on 143 F2:3 families. The genotypic data from these markers were then tested with the phenotypic data from inoculations in a single marker-trait analysis using PROC GLM (SAS institute, 1988). The results of the ANOVA indicated that the markers Satt595, Satt114, Satt334, Sat_317, Sat_197, Satt510, Satt335 and Satt144 on MLG F were significantly associated with the resistance phenotype (P<0.009). The markers on other MLGs did not show significant associations, indicating that the new resistance allele must be on MLG F (Table 6). (Soybase web site http://129.186.26.94).

Table 6 provides SSR markers used to identify markers associated with the resistance to *Phytophthora sojae* found in soybean PI399073. The significance values are from an analysis of variance (ANOVA) used to determine if the marker data was significantly associated with the phenotype following inoculations. The analysis for markers on MLGs A2 and F was performed in a population of 143 F2:3 lines. For all other linkage groups the analysis was performed on a subset of 94 F2:3 lines.

| Marker | MLG | Significance level |
|---|---|---|
| Satt252 | F | 0.38 |
| Satt516 | F | 0.05 |
| Satt425 | F | 0.55 |
| Satt595 | F | 0.009 |
| Satt114 | F | <0.0001 |
| Satt334 | F | <0.0001 |
| Sat_317 | F | <0.0001 |
| Sat_197 | F | 0.004 |
| Satt510 | F | <0.0001 |
| Satt335 | F | <0.0001 |
| Satt144 | F | 0.001 |
| Satt470 | A2 | 0.44 |
| Satt538 | A2 | 0.32 |
| Satt329 | A2 | 0.24 |
| Sat_310 | A2 | 0.09 |
| Sat_294 | A2 | 0.51 |
| Sat_347 | A2 | 0.14 |
| Sat_232 | A2 | 0.17 |
| Satt187 | A2 | 0.8 |
| Satt233 | A2 | 0.98 |
| Satt228 | A2 | 0.64 |
| Satt191 | G | 0.72 |
| Satt394 | G | 0.66 |
| Satt199 | G | 0.17 |
| Satt485 | N | 0.79 |
| Sat_091 | N | 0.93 |
| Satt545 | A1 | 0.98 |
| Satt182 | L | 0.84 |
| Satt243 | O | 0.86 |
| Satt231 | E | 0.91 |
| Satt380 | J | 0.11 |
| Satt440 | I | 0.8 |
| Satt387 | N | 0.14 |
| Satt216 | D1b + W | 0.17 |
| Satt509 | B1 | 0.34 |
| Satt267 | D1a + Q | 0.12 |

Table 7 provides a summary of the segregation and chi-square analysis of molecular markers on MLG F associated with resistance in F2:3 families of the cross Willams X PI399073. All markers listed are segregating as expected for a single Mendelian locus. WW=homozygous Williams allele, PP=homozygous PI399073 allele and WP=heterozygous. ns=not significant departure from the chi-square distribution.

| SSR Marker | WW | WP | PP | $X^2$ Value | Degrees of freedom |
|---|---|---|---|---|---|
| Satt516 | 33 | 73 | 22 | 4.4$^{ns}$ | 2 |
| Satt114 | 36 | 76 | 32 | 0.7$^{ns}$ | 2 |
| Satt334 | 35 | 74 | 33 | 0.3$^{ns}$ | 2 |
| Sat_317 | 34 | 67 | 42 | 1.5$^{ns}$ | 2 |
| Satt335 | 19 | 32 | 23 | 1.8$^{ns}$ | 2 |
| Satt510 | 25 | 54 | 37 | 3.0$^{ns}$ | 2 |
| Satt144 | 29 | 52 | 30 | 0.5$^{ns}$ | 2 |
| Sat_197 | 35 | 67 | 40 | 0.8$^{ns}$ | 2 |

Example 4

Linkage Map of MLG F of Soybean, Using SSR Markers, Providing Placement of Novel Trait Locus for Rps8 in Relation to Rps1-Rps7 on the Composite Soybean Genetic Map The crosses used for mapping the new allele were Williams (Rps) X PI399073 and S 19-90 (Rps1c) X PI399073. The $F_1$ plants from these crosses were selfed to produce populations of approximately 150 and 60 F2 plants for each cross, respectively. The F2 plants were then selfed and each plant was thrashed individually to yield seed for F2:3 families.

Analysis with SSR markers was performed as previously described.

Chi-square analysis was used for each DNA marker to test whether the F2:3 families fit the expected 1:2:1 ratio. DNA marker data that fit the expected ratio was then used in an ANOVA to determine if the marker data was significantly associated with resistance. ANOVAs were conducted using the GLM procedure in SAS (SAS institute, 1988). Once an SSR marker was found that was significantly associated with resistance, more SSR markers were tested from that area of the linkage group. Joinmap (Van Ooijen and Voorips, 2001) was then used to determine the order of the marker loci in the region of interest and the distances between them. Linkage group designations were made using mapped loci from the composite genetic linkage map (Cregan et al., 1999) and maintained on the Soybase web site (http://129.186.26.94 and http://soybase.ncgr.org/).

Example 5

Comparison of MLG F Linkage Map Between Two Different PI399073 Derived Hybrids (Williams x PI399073 and S 19-90 x PI399073) Confirming the Relative Placement of the Novel Locus for Rps8

In the past, numerous inoculations with different pathotypes of *P. sojae* were needed to confirm the presence of a new resistance allele in a number of soybean crosses. Mapping new alleles was also difficult due to the limited number of classical gene markers. SSR DNA marker technology has expedited this process of mapping a new gene with more precision. An additional cross with S 19-90 was used to confirm the presence of a new gene in contrast to earlier techniques that required developing multiple populations to test for allelism. The significant association with resistance of SSR markers from MLG F in the S 19-90 population provides confirmatory evidence of the location of Rps8.

S 19-90 was chosen to incorporate *Sclerotinia* stem rot resistance from S 19-90 as a step towards variety development. S 19-90 contains Rps1c so expectations for segregation ratios would be different from one locus to two loci.

The same procedures were used to map the new resistance gene in the cross S 19-90 X PI399073. First, ten F3 seedlings from each of 54 F2:3 families were inoculated with pathotype vir 7 (OH-race 1). The results of this inoculation fit a 15:1 ratio, which was expected due to the presence of both the new gene and Rps1c. Second, ten F3 seedlings were inoculated with vir 1a, 1b, 1c, 1k, 7 (OH-race 25). This inoculation also fit a 3:1 ratio, 38 F2:3 families that were scored as resistant and 16 were scored as susceptible ($\chi2=0.61$).

The SSR markers on MLG F found to be polymorphic in the first cross were tested on the parents of the second cross S 19-90 X PI399073. Satt114 and Satt334 were also polymorphic for this cross. Other SSR markers from MLG F were tested with S 19-90 and PI399073 and Sat__229 was found to be polymorphic as well.

All of the polymorphic markers for S 19-90 and PI399073 were used in single-factor ANOVAs. The markers Satt114, Sat__334 and Sat__229 on MLG F were associated with the resistance phenotype in the S 19-90 population (P<0.05).

Example 6

Introgression to Produce HFX01-602

F1 plants of HFX01-602 were grown in the OARDC greenhouse at Wooster, Ohio and tested for the presence of Rps8 from PI399.073. Remnant seed from plants that were segregating or homozygous for Rps8 were bulked to create seeds deposited as HFX01-602.

F3 seed were single-plant harvested from four plants. Seed of all of the plants were evaluated for the presence for Rps8 by inoculation with a *Phytophthora sojae* isolate with following pathotype (1a, 1b, 1c, 1k, 3a, 3c, 4, 5, 6, 7). Kottman has genes Rps1k and Rps3a with high levels of partial resistance and NK S19-90 has Rps1c. No *P. sojae* isolate is currently known that can differentially kill plants with Rps8 in a consistent fashion, so there is no means to identify if these other Rps genes are present or segregating in these lines.

Table 9 shows Phenotypic analysis of F2:3 lines of OX01-602 soybean lines for resistance to *P. sojae* pathotype (vir 1a, 1b, 1c, 1k, 3a, 3c, 4, 5, 6, 7) for the number of lines that are homozygous resistant compared to the number of lines that are segregating and homozygous susceptible.

TABLE 8

| OX01-602 | $F_1$ plant | $F_2$ plant | Rps8Rps8:Total |
| --- | --- | --- | --- |
| | 3 | 1 | 5:39 |
| | 3 | 3 | 4:34 |
| | | (no molecular data) | |
| | 4 | 1 | None |
| | 4 | 2 | 17:41 |

What is claimed is:

1. A method for determining if a soybean has Rps8-derived *Phytophthora sojae* resistance, comprising:
    (a) analyzing genomic DNA from the soybean for the presence of a combination of molecular markers on major linkage group F which are associated with trait locus Rps8, whereby detecting the presence of the molecular markers provides an indication that said Rps8-derived *P. sojae* resistance is present in the soybean; and
    (b) confirming that the soybean has Rps8-derived *P. sojae* resistance by inoculating the soybean with one or a combination of *P. sojae* pathotypes vir1a, 1b, 1c, 1d, 1k, 2, 3a, 3b, 3c, 4, 5, 6 or 7 to which the soybean would be susceptible if the soybean did not have Rps8-derived *P. sojae* resistance;
    wherein Rps8-derived *P. sojae* resistance confers resistance to all *P. sojae* pathotypes vir1a, 1b, 1c, 1d, 1k, 2, 3a, 3b, 3c, 4, 5, 6 and 7.

2. The method of claim 1 wherein the molecular markers are selected from the group consisting of Satt516, Satt595, Satt114, Satt334, Sat__317, $Sat_{13}$ 197, Satt510, Satt335 and Satt144.

3. The method of claim 1 wherein the molecular markers are markers Satt516 and Satt 114.

4. The method of claim 1, wherein the soybean is a progeny resulting from a cross between two parents wherein at least one parent has Rps8-derived *P. sojae* resistance.

5. The method of claim 4, wherein the at least one parent that has Rps8-derived *P. sojae* resistance is a soybean of plant line PI 399073 or a descendant thereof.

6. A method of selecting a soybean plant having Rps8-derived *Phytophthora sojae* resistance, comprising:

(a) providing a soybean plant that is a progeny from a cross between a first parent that has Rps8-derived *P. sojae* resistance and a second parent that does not have Rps8-derived *P. sojae* resistance;

(b) detecting in the first parent a first nucleic acid which is genetically linked to trait locus Rps8, wherein trait locus Rps8 is mapped to a locus on major linkage group F that is located between molecular markers Satt114 and Satt516; and (c) identifying a soybean plant as having trait locus Rps8 by screening the soybean plant for the presence of the first nucleic acid (d) inoculating the soybean plant identified as having trait locus Rps8 with one or a combination of *P. sojae* pathotypes vir1a, 1b, 1c, 1d, 1k, 2, 3a, 3b, 3c, 4, 5, 6 or 7 to which the soybean plant would otherwise be susceptible if the soybean plant did not have Rps8-derived *P. sojae* resistance to confirm that the soybean plant has Rps8-derived *P. sojae* resistance;

wherein Rps8-derived *P. sojae* resistance confers resistance to all *P. sojae* pathotypes vir1a, 1b, 1c, 1d, 1k, 2, 3a, 3b, 3c, 4, 5, 6 and 7; and, (e) selecting the soybean plant that has been identified as having the Rps8 trait locus and that has been confirmed as having Rps8-derived *P. sojae* resistance.

7. The method of claim 6, wherein the first nucleic acid is a marker selected from the group consisting of:

(a) Satt 114, Satt 516, Satt595, Satt334, Sat_317 Sat_197, Satt510, Satt335, Satt144; and (b) a marker linked to a marker of (a).

8. The method of claim 6, wherein detecting the first nucleic acid comprises microsatellite analysis.

9. The method of claim 6, wherein detecting the first nucleic acid comprises hybridization of a second nucleic acid to the first nucleic acid.

10. The method of claim 6, wherein the first parent is a soybean of plant line PI 399073 or a descendant thereof.

11. The method of claim 6, wherein Rps8-derived resistance is derived from the plant line HFX01-602 or a descendant thereof.

12. A method of identifying soybean plants that are likely to have trait locus Rps8, the method comprising:

(a) detecting a first locus on the genome of the plant which is genetically linked to trait locus Rps8, wherein the first locus maps to major linkage group F and is located between molecular marker Satt114 and Satt516; and (b) determining that the soybean plant does not have Rps3.

13. The method of claim 12, wherein the first locus is linked to a marker selected from the group consisting of Satt595, Satt334, Sat_317, Sat_197, Satt510, Satt335, and Satt144.

14. A method of selecting a soybean plant having Rps8-derived *Phytophthora sojae* resistance, comprising:

(a) producing a progeny from a cross between a first parent that has Rps8-derived *P. sojae* resistance and a second parent that does not have Rps8-derived *P. sojae* resistance;

(b) detecting a *P. sojae* isolate that the second parent is susceptible to, wherein said *P. sojae* isolate is selected from the group consisting of pathotypes vir1a, 1b, 1c, 1d, 1k, 2, 3a, 3b, 3c, 4, 5, 6, 7, and combinations thereof; and (c) selecting the progeny that is resistant to said *P. sojae* isolate, thereby selecting a soybean plant having Rps8-derived *P sojae* resistance.

15. The method of claim 14, wherein the *P. sojae* isolate is selected from the group consisting of *P. sojae* race 1, race 4, race 17, race 25, race 30, and combinations thereof.

16. The method of claim 14, wherein the first parent is a plant variety selected from the group consisting of HFX01-602, OX-98317, OX-99218, OX-99128 or descendants thereof.

17. The method of claim 6, wherein the first parent is a plant variety selected from the group consisting of OX-98317, OX-99218, OX-99128 or descendants thereof.

18. The method of claim 6, wherein the Rps8 derived *P. sojae* resistance of the first parent is determined by inoculation of the first parent with one or more *P. sojae* pathotypes selected from the group consisting of pathotypes vir1a, 1b, 1c, 1d, 1k, 2, 3a, 3b, 3c, 4, 5, 6, 7, and combinations thereof.

19. The method of claim 4, wherein the at least one parent that has Rps8 derived *P. sojae* resistance is a plant variety selected from the group consisting of HFX01-602, OX-98317, OX-99218, OX-99128 or descendants thereof.

20. The method of claim 1, wherein step b comprises selecting for inoculation of the soybean a *P. sojae* isolate to which a parent of the soybean that lacks Rps8-derived *P. sojae* resistance is susceptible and inoculating the soybean with said isolate to confirm that the soybean has Rps8-derived *P. sojae* resistance.

21. The method of claim 1, wherein step b comprises inoculating the soybean with a *P. sojae* pathotype that has virulence to Rps3a, Rps3b, or Rps3c, but not Rps8.

22. The method of claim 1, wherein step b comprises inoculating the soybean with *P. sojae* race 7 or 17.

23. The method of claim 1, further comprising the step of determining that the soybean is a progeny from parents that lack Rps3.

24. The method of claim 6, wherein step d comprises inoculating the soybean having trait locus Rps8 with a *P. sojae* isolate to which a parent of the soybean is susceptible.

25. The method of claim 6, wherein step d comprises inoculating the soybean having trait locus Rps8 with a *P. sojae* pathotype that has virulence to Rps3a, Rps3b, or Rps3c, but not Rps8.

26. The method of claim 6, wherein step d comprises inoculating the soybean having trait locus Rps8 with *P. sojae* race 7 or 17.

27. The method of claim 6, further comprising the step of determining that the soybean is a progeny from parents that lack Rps3.

28. The method of claim 12, wherein step b comprises inoculating the soybean with a *P. sojae* pathotype that has virulence to Rps3a, Rps3b, or Rps3c, but not Rps8.

29. The method of claim 12, wherein step b comprises inoculating the soybean with *P. sojae* race 7 or 17.

30. The method of claim 12, wherein step b further comprises determining that the soybean is a progeny from parents that lack Rps3.

* * * * *